(12) United States Patent
Yabe

(10) Patent No.: US 12,357,540 B2
(45) Date of Patent: Jul. 15, 2025

(54) SYRINGE-SHAPED SPRAYING DEVICE

(71) Applicant: NIPRO CORPORATION, Osaka (JP)

(72) Inventor: Yukihiro Yabe, Osaka (JP)

(73) Assignee: NIPRO CORPORATION, Osaka (JP)

( * ) Notice: Subject to any disclaimer, the term of this patent is extended or adjusted under 35 U.S.C. 154(b) by 520 days.

(21) Appl. No.: 17/774,190

(22) PCT Filed: Nov. 5, 2020

(86) PCT No.: PCT/JP2020/041336
§ 371 (c)(1),
(2) Date: May 4, 2022

(87) PCT Pub. No.: WO2021/090876
PCT Pub. Date: May 14, 2021

(65) Prior Publication Data
US 2022/0370294 A1  Nov. 24, 2022

(30) Foreign Application Priority Data

Nov. 6, 2019  (JP) .................................. 2019-201328

(51) Int. Cl.
*A61J 1/20*  (2006.01)
*A61M 31/00*  (2006.01)

(52) U.S. Cl.
CPC ............. *A61J 1/2096* (2013.01); *A61J 1/201* (2015.05); *A61J 1/2065* (2015.05); *A61M 31/00* (2013.01); *A61M 2210/0618* (2013.01)

(58) Field of Classification Search
CPC ........ A61J 1/2096; A61J 1/201; A61J 1/2065; A61M 31/00; A61M 2205/073;
(Continued)

(56) References Cited

U.S. PATENT DOCUMENTS 3,874,380 A   4/1975  Baum
3,874,381 A   4/1975  Baum
(Continued)

FOREIGN PATENT DOCUMENTS

JP          3047521 U    4/1998
JP       2001-137344 A   5/2001
(Continued)

OTHER PUBLICATIONS

Japanese Office Action dated May 9, 2023 in Application No. 2019-201328.
(Continued)

*Primary Examiner* — Susan S Su
*Assistant Examiner* — Erin A Kim
(74) *Attorney, Agent, or Firm* — Sughrue Mion, PLLC

(57) ABSTRACT

A syringe-shaped spraying device includes: a syringe-shaped spraying device main body including a barrel that stores a liquid medicine, a plunger having a front end inserted in the barrel with a gasket being attached to the front end, and a nozzle that is provided with a spraying hole for spraying the liquid medicine and that is connected to a front end of the barrel; a vial adapter having a transfer needle to pierce a vial that stores a liquid medicine so as to suction the liquid medicine; and a connection adapter that is attached to the syringe-shaped spraying device main body and that connects the vial adapter to the syringe-shaped spraying device main body.

3 Claims, 16 Drawing Sheets

(58) Field of Classification Search
CPC .......... A61M 2205/19; A61M 11/007; A61M 2210/0618; A61M 2039/1027; A61M 39/1011
See application file for complete search history.

(56) References Cited

U.S. PATENT DOCUMENTS

| | | | | |
|---|---|---|---|---|
| 4,493,348 | A * | 1/1985 | Lemmons | A61J 7/0053 |
| | | | | 215/11.1 |
| 4,516,967 | A * | 5/1985 | Kopfer | A61J 1/2096 |
| | | | | 604/87 |
| 6,427,680 | B1 | 8/2002 | Oechsel | |
| 2002/0174864 | A1 * | 11/2002 | Alchas | A61M 15/0025 |
| | | | | 128/200.14 |
| 2011/0004185 | A1 * | 1/2011 | Hasegawa | A61J 1/2096 |
| | | | | 604/411 |
| 2013/0096493 | A1 * | 4/2013 | Kubo | A61M 3/0262 |
| | | | | 604/212 |
| 2018/0028402 | A1 * | 2/2018 | Kriheli | A61J 1/2013 |
| 2020/0030552 | A1 | 1/2020 | Yabe et al. | |

FOREIGN PATENT DOCUMENTS

| | | |
|---|---|---|
| JP | 2002-510225 A | 4/2002 |
| JP | 2014-140588 A | 8/2014 |
| WO | 2012/002398 A1 | 1/2012 |
| WO | 2018/186277 A1 | 10/2018 |
| WO | 2019/004128 A1 | 1/2019 |

OTHER PUBLICATIONS

Extended European Search Report issued Oct. 24, 2023 in European Application No. 20884218.7.
International Search Report for PCT/JP2020/041336 dated Jan. 19, 2021.

\* cited by examiner

SYRINGE-SHAPED SPRAYING DEVICE

CROSS REFERENCE TO RELATED APPLICATIONS

This application is a National Stage of International Application No. PCT/JP2020/041336, filed Nov. 5, 2020, claiming priority to Japanese Patent Application No. 2019-201328, filed Nov. 6, 2019.

TECHNICAL FIELD

The present disclosure relates to a syringe-shaped spraying device.

BACKGROUND ART

A syringe-shaped spraying device described in Japanese Patent Laying-Open No. 2001-137344 (PTL 1) is an exemplary, conventional syringe-shaped spraying device. Such a conventional syringe-shaped spraying device as described in PTL 1 is delivered with its syringe being supplied with a liquid medicine in advance (for example, paragraph 0001 of PTL 1).

CITATION LIST

Patent Literature

PTL 1: Japanese Patent Laying-Open No. 2001-137344

SUMMARY OF INVENTION

Technical Problem

The conventional syringe-shaped spraying device has a structure that is based on such a premise that the syringe is supplied with the liquid medicine in advance. In the syringe-shaped spraying device of PTL 1, no medicine can be suctioned from its nozzle. In the syringe-shaped spraying device of PTL 1, a valve is provided inside the nozzle to restrict a liquid medicine from flowing from the front end side of the nozzle toward the base end side of the nozzle.

An object of the present disclosure is to provide a syringe-shaped spraying device in which a syringe can be supplied with a liquid medicine by suctioning the liquid medicine from a nozzle.

Solution to Problem

A syringe-shaped spraying device according to the present disclosure includes: a syringe-shaped spraying device main body including a barrel that stores a liquid medicine, a plunger having a front end inserted in the barrel with a gasket being attached to the front end, and a nozzle that is provided with a spraying hole for spraying the liquid medicine and that is connected to a front end of the barrel; a vial adapter having a transfer needle to pierce a vial that stores a liquid medicine so as to suction the liquid medicine; and a connection adapter that is attached to the syringe-shaped spraying device main body and that connects the vial adapter to the syringe-shaped spraying device main body.

In the syringe-shaped spraying device, the connection adapter may have a guide extending in a direction orthogonal to a direction in which the nozzle extends.

In the syringe-shaped spraying device, a depression may be formed between a rear end of the nozzle and the barrel, and the connection adapter has an engagement protrusion protruding toward the depression, and the connection adapter may be locked to the syringe-shaped spraying device main body with the engagement protrusion being engaged with the rear end of the nozzle.

In the syringe-shaped spraying device, the connection adapter may have a threaded portion, and the vial adapter may be connected to the connection adapter using the threaded portion.

Advantageous Effects of Invention

According to the present disclosure, there can be provided a syringe-shaped spraying device in which a syringe can be supplied with a liquid medicine by suctioning the liquid medicine from a nozzle.

DESCRIPTION OF EMBODIMENTS

Hereinafter, embodiments of the present disclosure will be described in detail with reference to figures. A syringe-shaped spraying device according to an embodiment described below is a transnasal administration device for administering, to a pair of nasal cavities of a patient, a liquid medicine suctioned from a vial.

Figure 1:
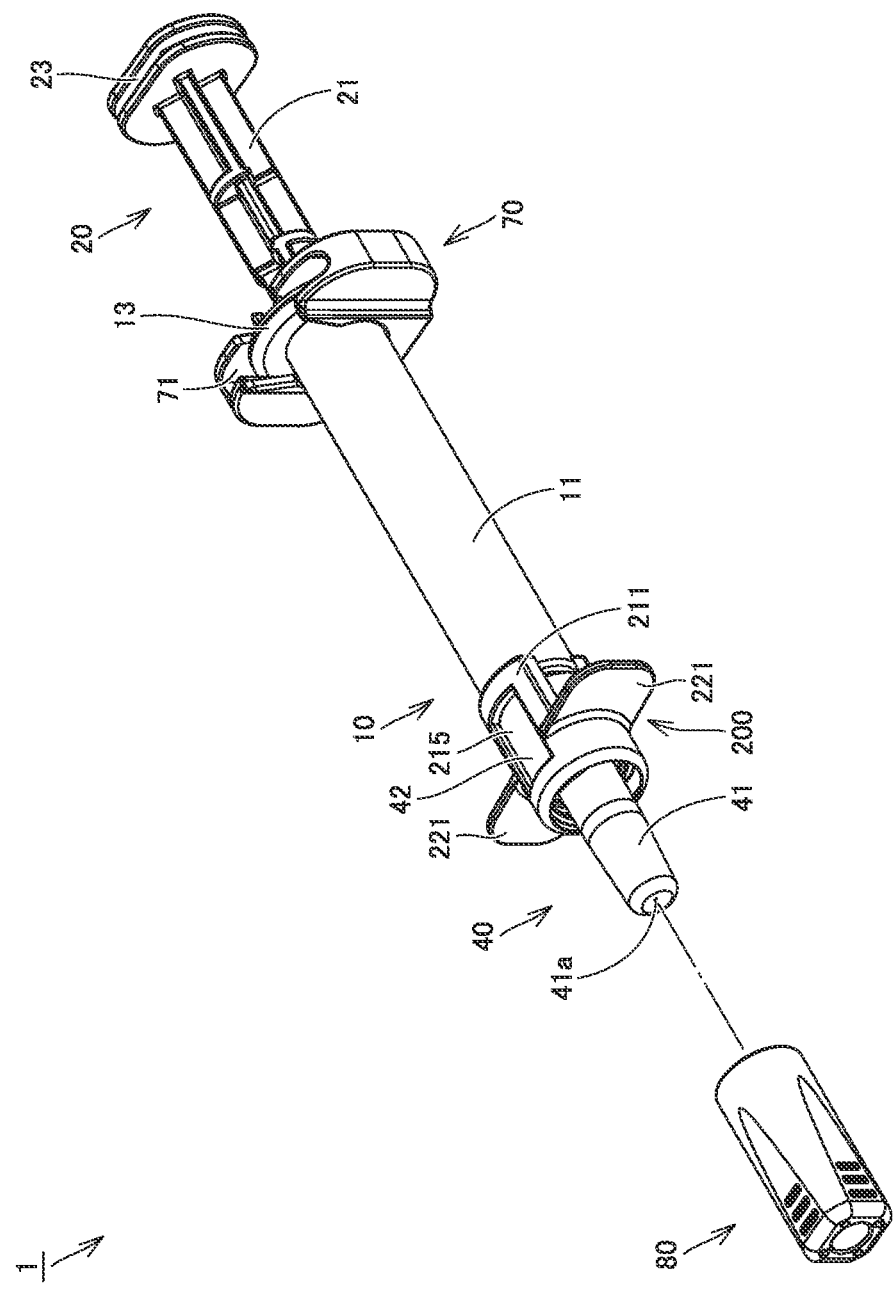
FIG. 1 is a perspective view of a syringe-shaped spraying device.
Figure 2:
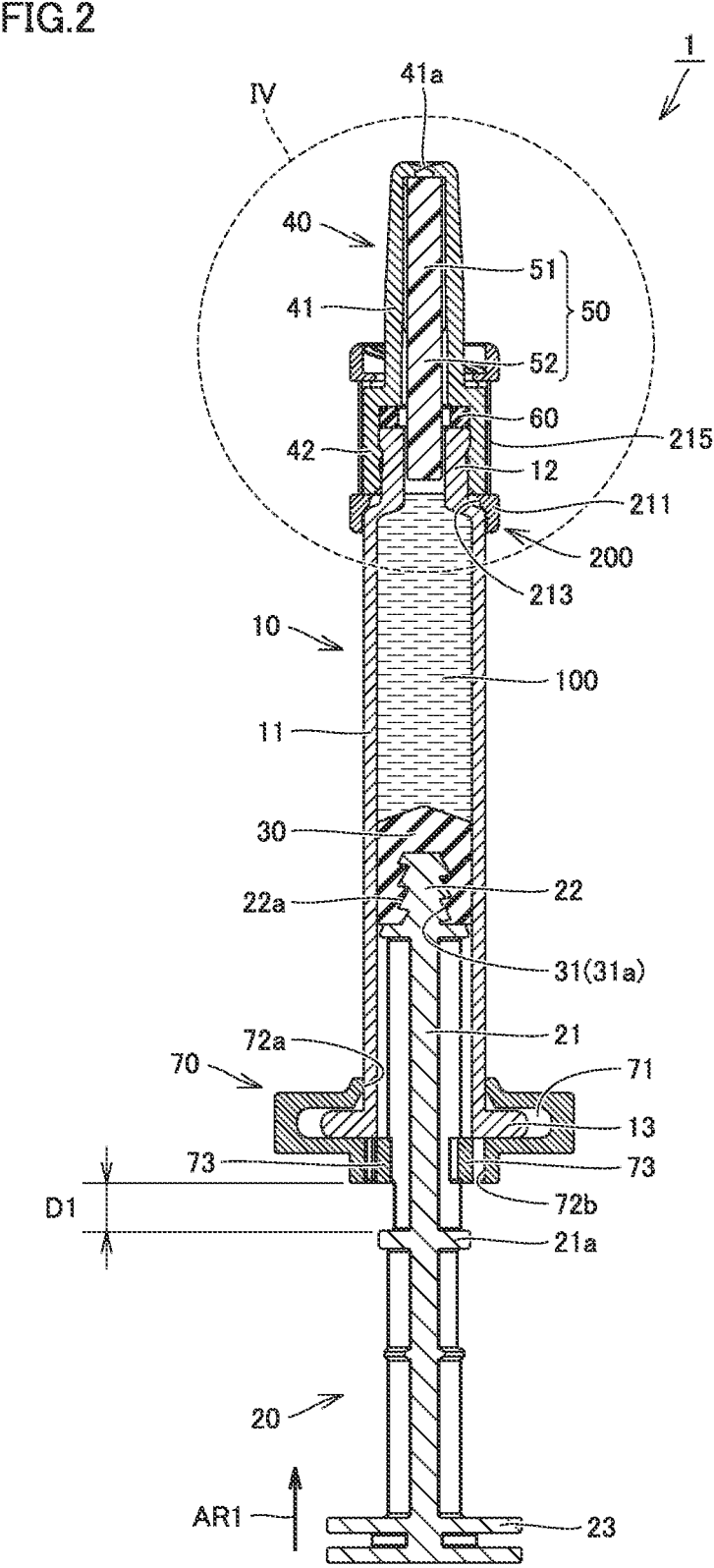
FIG. 2 is a cross sectional view of the syringe-shaped spraying device.
Figure 3:
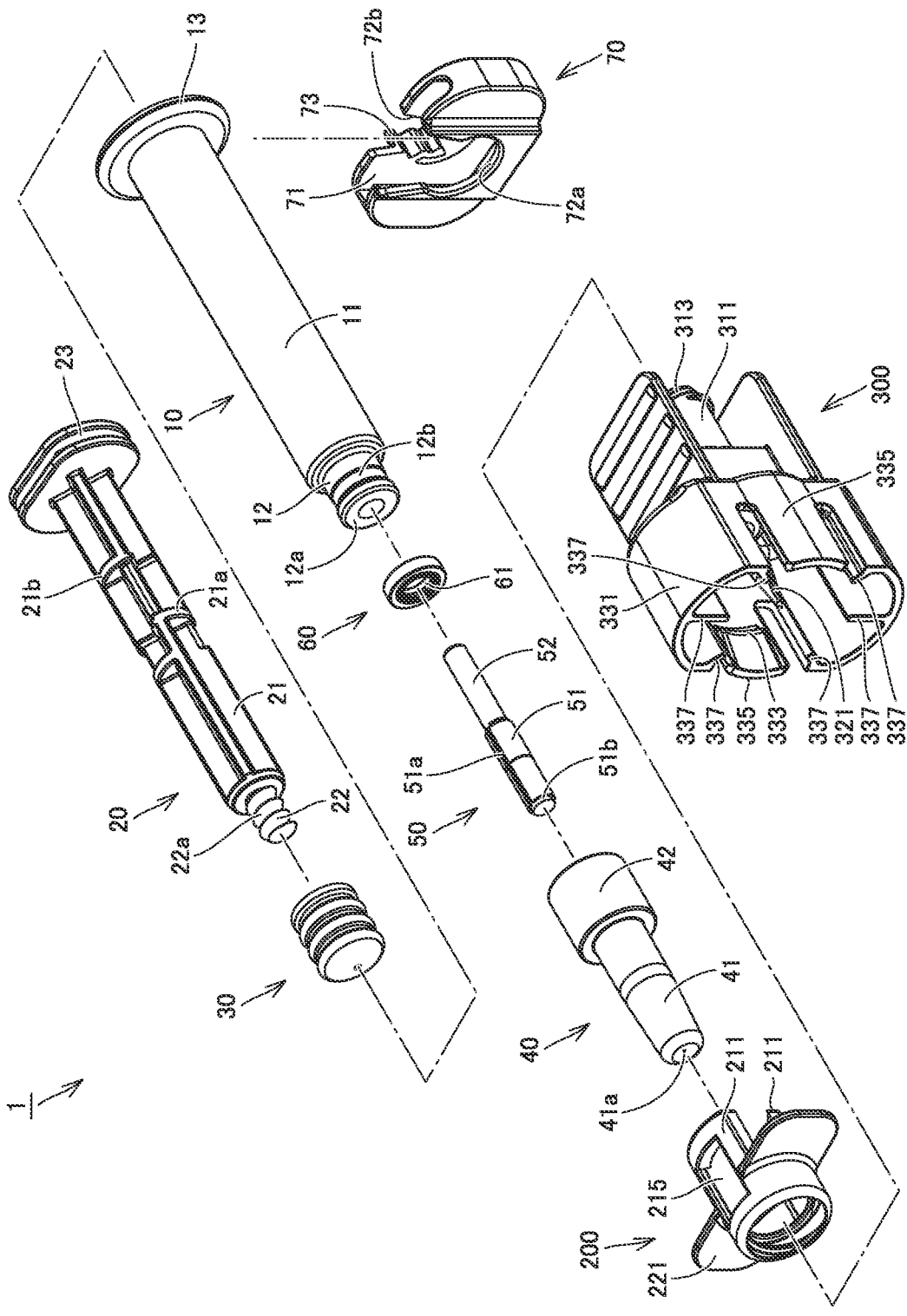
FIG. 3 is an exploded perspective view of the syringe-shaped spraying device.

FIG. 1 is a perspective view of a syringe-shaped spraying device according to an embodiment of the present disclosure. FIG. 2 is a cross sectional view of the syringe-shaped spraying device. In FIGS. 1 and 2, no vial adapter is illustrated. FIG. 3 is an exploded perspective view of the syringe-shaped spraying device. First, referring to FIGS. 1 to 3, a schematic configuration of a syringe-shaped spraying device 1 according to the present embodiment will be described.

The following first describes a structure of the syringe-shaped spraying device having the liquid medicine suctioned therein and a method of administering the liquid medicine, and then describes a structure of the syringe-shaped spraying device to which a vial adapter is attached and a method of suctioning the liquid medicine. It should be noted that the syringe-shaped spraying device of the present disclosure includes the vial adapter; however, in the description below, the syringe-shaped spraying device in a state in which the vial adapter is attached thereto and the syringe-shaped spraying device in a state in which no vial adapter attached is thereto are both referred to as "syringe-shaped spraying device".

As shown in FIGS. 1 to 3, syringe-shaped spraying device 1 has an elongated bar-like shape as a whole, and mainly includes a barrel 10, a plunger 20, a gasket 30, a nozzle 40, a core 50, a packing 60, a finger grip 70, a cap 80, a connection adapter 200, and a vial adapter 300. A syringe-shaped spraying device main body includes barrel 10, plunger 20, and nozzle 40. FIG. 2 shows syringe-shaped spraying device 1 (syringe-shaped spraying device main body) having a liquid medicine 100 suctioned therein.

Barrel 10 is constituted of an elongated, substantially cylindrical member having open ends in the axial direction, and includes a tubular portion 11, a connecting portion 12, and a flange portion 13. Tubular portion 11 is constituted of a region having a cylindrical shape and extending along the axial direction. Connecting portion 12 is located at the front end of tubular portion 11, and is constituted of a decreased-diameter portion having a tubular shape and formed to have an outer diameter and an inner diameter smaller than those of tubular portion 11. Flange portion 13 is located at the rear end of tubular portion 11, and is constituted of an increased-diameter portion formed to have an outer diameter larger than that of tubular portion 11.

Barrel 10 has a hollow, cylindrical space therein, and gasket 30 is accommodated in the space. In the space formed in barrel 10, liquid medicine 100 can be supplied into a space on the front end side of barrel 10 with respect to a portion at which gasket 30 is located. In a space on the rear end side of barrel 10 with respect to the portion at which gasket 30 is located, the front end of plunger 20 for pushing gasket 30 is inserted.

A material of barrel 10 is appropriately selected depending on a type of liquid medicine 100 to be suctioned. Barrel 10 is desirably constituted of glass or constituted of an injection-molded product employing a resin material as a raw material. Barrel 10 is preferably transparent or translucent, and barrel 10 may be provided with a scale indicating a remaining amount of liquid medicine 100.

Plunger 20 is constituted of an elongated bar-like member, and includes a rod portion 21, a coupler portion 22, and a flange portion 23. Rod portion 21 is constituted of a region that extends along the axial direction and that has a cross section substantially in the form of a cross. Coupler portion 22 is provided to protrude from the front end of rod portion 21 along the axial direction of plunger 20, and has an outer circumferential surface provided with an external thread 22a. Flange portion 23 is constituted of a region that is substantially in the form of a plate and that includes a portion protruding from the rear end of rod portion 21 in a direction orthogonal to the axial direction of plunger 20.

The front end of plunger 20 is inserted from the rear end of barrel 10 to the inside of barrel 10. Plunger 20 is pushed by a user to move plunger 20 relative to barrel 10, with the result that gasket 30 is moved in barrel 10 to spray liquid medicine 100 from syringe-shaped spraying device 1.

Plunger 20 is desirably constituted of an injection-molded product employing a resin material as a raw material. It should be noted that a first abutment portions 21a and a second abutment portions 21b both protruding from the circumferential surface of rod portion 21 are provided at predetermined positions in the axial direction of plunger 20, and first abutment portions 21a and second abutment portions 21b will be described later.

Gasket 30 is constituted of a member having a substantially cylindrical shape, and is provided with an axial hole portion 31 at the rear end thereof in the axial direction. An internal thread 31a is provided in an inner circumferential surface of gasket 30. The inner circumferential surface defines axial hole portion 31.

Coupler portion 22 of plunger 20 is inserted in axial hole portion 31 of gasket 30. An external thread 22a provided in the outer circumferential surface of coupler portion 22 of plunger 20 is screwed into internal thread 31a provided in the inner circumferential surface of gasket 30 defining axial hole portion 31. Thus, gasket 30 is fixed to the front end of plunger 20 and is therefore attached to plunger 20.

Gasket 30 is accommodated in tubular portion 11 of barrel 10 in a slidable manner. More specifically, the outer circumferential surface of gasket 30 is in close contact with the inner circumferential surface of tubular portion 11 of barrel 10 such that the outer circumferential surface of gasket 30 is slidable on the inner circumferential surface of tubular portion 11 of barrel 10. Accordingly, liquid medicine 100 in barrel 10 is prevented from leaking to the plunger 20 side.

A material of gasket 30 is appropriately selected depending on a type of liquid medicine 100. Gasket 30 is desirably constituted of a rubber elastic body. Examples of the rubber elastic body usable herein include a butyl rubber, a butadiene rubber, an isoprene rubber, a silicone rubber, a thermoplastic elastomer, a silicone elastomer, and the like.

Nozzle 40 is constituted of a member having a substantially cylindrical shape with a bottom, and has a nozzle portion 41 and a connected portion 42. Nozzle portion 41 includes: a region having a substantially cylindrical shape and extending along the axial direction; and a bottom portion that closes the front end of the portion having the substantially cylindrical shape. A spraying hole 41a having a minute opening diameter is provided in the bottom portion. Connected portion 42 is located at the rear end of nozzle portion 41 and is constituted of an increased-diameter portion formed to have an outer diameter and an inner diameter larger than those of nozzle portion 41.

Nozzle 40 has a hollow, substantially cylindrical space therein, and connecting portion 12 of barrel 10, core 50 and packing 60 are accommodated in the space. Connecting portion 12 and packing 60 are located inside connected portion 42, and core 50 is located inside both nozzle portion 41 and connected portion 42.

Connecting portion 12 of barrel 10 is inserted into connected portion 42 of nozzle 40 from the rear end side of nozzle 40. Thus, nozzle 40 is connected to the front end of barrel 10. Specifically, since the inner diameter of connected portion 42 is slightly smaller than the outer diameter of connecting portion 12, nozzle 40 is connected to barrel 10 by press-fitting connecting portion 12 into connected portion 42. It should be noted that a more detailed connection structure between barrel 10 and nozzle 40 will be described later.

Nozzle 40 sprays, to outside, liquid medicine 100 suctioned to barrel 10. Nozzle 40 has a flow path through which liquid medicine 100 flows during use. Nozzle 40 is provided with spraying hole 41a for spraying, to the outside, liquid medicine 100 having flowed through the flow path.

Here, although details will be described later, the flow path for liquid medicine 100 inside nozzle 40 has a sufficiently small cross sectional area because core 50 is disposed inside nozzle 40. Accordingly, when plunger 20 is pushed into barrel 10 during use, the pressure of liquid medicine 100 is increased in the flow path, with the result that liquid medicine 100 is sprayed in the form of a mist from spraying hole 41a provided in nozzle 40.

On the other hand, in the flow path formed by nozzle 40 and core 50, there is no object that blocks liquid medicine 100 from flowing in the direction from the front end of nozzle 40 to barrel 10. Therefore, in the flow path formed by nozzle 40 and core 50, liquid medicine 100 can flow in the direction from the front end of nozzle 40 to barrel 10.

A material of nozzle 40 is appropriately selected depending on a type of liquid medicine 100. Nozzle 40 is desirably constituted of an injection-molded product employing a resin material as a raw material.

Core 50 is constituted of a member having a substantially cylindrical shape, and has a large-diameter portion 51 located on the front end side and a small-diameter portion 52 located on the rear end side. The outer diameter of large-diameter portion 51 is substantially equal to the inner diameter of nozzle portion 41 of nozzle 40, and the outer diameter of small-diameter portion 52 is smaller than the inner diameter of nozzle portion 41 of nozzle 40.

First groove portions 51a extending along the axial direction are provided in the outer circumferential surface of large-diameter portion 51, and second groove portions 51b extending along the circumferential direction are provided in the front end of large-diameter portion 51. End portions of first groove portions 51a on the front end side of core 50 are connected to second groove portions 51b.

A material of core 50 is appropriately selected depending on a type of liquid medicine 100. Core 50 is desirably constituted of an injection-molded product employing a resin material as a raw material.

As described above, core 50 is accommodated inside nozzle 40 and the flow path for liquid medicine 100 is defined between core 50 and nozzle 40. Details thereof will be described later.

Packing 60 is constituted of an annular member provided with a through hole 61 extending therethrough in the axial direction, and is accommodated inside connected portion 42 of nozzle 40 as described above. Packing 60 is interposed between barrel 10 and nozzle 40, more specifically, is located between connecting portion 12 of barrel 10 and connected portion 42 of nozzle 40. Thus, packing 60 functions as a sealing member that prevents liquid medicine 100 from leaking from between barrel 10 and nozzle 40.

A material of packing 60 is appropriately selected depending on a type of liquid medicine 100. Packing 60 is desirably constituted of a rubber elastic body. Examples of the rubber elastic body usable herein include a butyl rubber, a butadiene rubber, an isoprene rubber, a silicone rubber, a thermoplastic elastomer, a silicone elastomer, and the like. Alternatively, packing 60 may be constituted of a resin member having an appropriate degree of elasticity instead of the rubber elastic body.

Finger grip 70 has a flat box-like shape with an accommodation space 71 being formed therein and with a slit-like opening being provided at a side portion thereof. Finger grip 70 has a pair of wall portions located along the axial direction of barrel 10. Of the pair of wall portions, a wall portion located on the front end side is provided with a first insertion portion 72a in which tubular portion 11 of barrel 10 is inserted and through which tubular portion 11 of barrel 10 extends. Of the pair of wall portions, a wall portion located on the rear end side is provided with a second insertion portion 72b in which rod portion 21 of plunger 20 is inserted and through which rod portion 21 of plunger 20 extends.

Finger grip 70 is attached to flange portion 13 of barrel 10. More specifically, finger grip 70 can be assembled to barrel 10 so as to accommodate flange portion 13 in accommodation space 71 through the slit-like opening provided at the side portion of finger grip 70.

Finger grip 70 is a region to be held by fingers of the user when pushing plunger 20 into barrel 10. It should be noted that finger grip 70 is constituted of, for example, an injection-molded product employing a resin material as a raw material.

Stoppers 73 each having a protruding shape are provided at second insertion portion 72b of finger grip 70. Stoppers 73 can be brought into abutment with first abutment portions 21a and second abutment portions 21b provided at rod portion 21 of plunger 20.

Here, first abutment portions 21a provided at plunger 20 are fan-shaped regions provided to connect a pair of adjacent wall portions of four wall portions located in the circumferential direction of rod portion 21 that is in the form of a cross when viewed in a cross section. In the present embodiment, a pair of first abutment portions 21a are provided at a pitch of 180° in the circumferential direction of rod portion 21.

Likewise, second abutment portions 21b provided at plunger 20 are fan-shaped portions provided to connect a pair of adjacent wall portions of the four wall portions located in the circumferential direction of rod portion 21 that is in the form of a cross when viewed in a cross section. In the present embodiment, a pair of second abutment portions 21b are provided at a pitch of 180° in the circumferential direction of rod portion 21.

The pair of second abutment portions 21b are provided at positions on the rear end side of plunger 20 with respect to the portions at which the pair of first abutment portions 21a are provided. The pair of second abutment portions 21b are provided at positions not overlapping with the pair of first abutment portions 21a in the axial direction of rod portion 21.

On the other hand, stoppers 73 provided at finger grip 70 protrude inwardly from an edge portion of second insertion portion 72b. A pair of stoppers 73 are provided at a pitch of 180° along the circumferential direction of second insertion portion 72b.

Thus, in a state in which the pair of first abutment portions 21a and the pair of stoppers 73 overlap with each other in the axial direction of plunger 20, the pair of first abutment portions 21a and the pair of stoppers 73 are brought into abutment with each other when plunger 20 is pushed, with the result that the pushing of plunger 20 is stopped. On the other hand, in a state in which the pair of first abutment portions 21a and the pair of stoppers 73 do not overlap with each other in the axial direction of plunger 20, the pair of first abutment portions 21a and the pair of stoppers 73 are not brought into abutment with each other when plunger 20 is pushed, with the result that the pushing of plunger 20 is not stopped.

Likewise, in a state in which the pair of second abutment portions 21b and the pair of stoppers 73 overlap with each other in the axial direction of plunger 20, the pair of second abutment portions 21b and the pair of stoppers 73 are brought into abutment with each other when plunger 20 is pushed, with the result that the pushing of plunger 20 is stopped. On the other hand, in a state in which the pair of second abutment portions 21b and the pair of stoppers 73 do not overlap with each other in the axial direction of plunger 20, the pair of second abutment portions 21b and the pair of stoppers 73 are not brought into abutment with each other when plunger 20 is pushed, with the result that the pushing of plunger 20 is not stopped.

Therefore, by rotating plunger 20 in the circumferential direction with respect to the axis of plunger 20 with the front end of plunger 20 being inserted in barrel 10, movement of plunger 20 becomes restricted or unrestricted by finger grip 70. Hence, by appropriately adjusting the positions of first abutment portions 21a and second abutment portions 21b provided at plunger 20, an amount of liquid medicine 100 to be administered by one pushing operation on plunger 20 can be adjusted to a predetermined amount.

Cap 80 has a substantially polygonal tubular shape with a bottom, and is detachably attached to nozzle 40. Cap 80 is attached to nozzle 40 so as to cover nozzle portion 41 of nozzle 40 when syringe-shaped spraying device 1 is not in use. Thus, when syringe-shaped spraying device 1 is not in use, the vicinity of spraying hole 41a provided in nozzle 40 is kept clean by cap 80.

A material of cap 80 is appropriately selected depending on a type of liquid medicine 100. Cap 80 is desirably constituted of a rubber elastic body. Examples of the rubber elastic body usable herein include a butyl rubber, a butadiene rubber, an isoprene rubber, a silicone rubber, a thermoplastic elastomer, a silicone elastomer, and the like. Further, cap 80 may be constituted of a resin member having an appropriate degree of elasticity instead of the rubber elastic body.

As shown in FIGS. 1 to 3, connection adapter 200 mainly has: a pair of guides 221 extending outward; a pair of engagement segments 211 extending rearward; and a pair of engagement protrusions 213 provided at the rear end of engagement segments 211 and protruding inward. The pair of guides 221 are located symmetrically with respect to the central axis of nozzle 40. Each of guides 221 has a plate-like shape.

Guide 221 is provided to prevent nozzle 40 from being inserted too deep in a nasal cavity when spraying the liquid medicine into the nasal cavity. Therefore, the position of guide 221 is set to a position suitable for that purpose. Guide 221 is not necessarily required to have the plate-like shape, and may have any shape as long as it functions as a guide when brought into abutment with the outer circumferential portion of the nasal cavity. Further, it is not necessarily required to provide a pair of guides 221. A guide 221 may extend continuously on the outer circumferential portion in the form of a flange.

Figure 4:
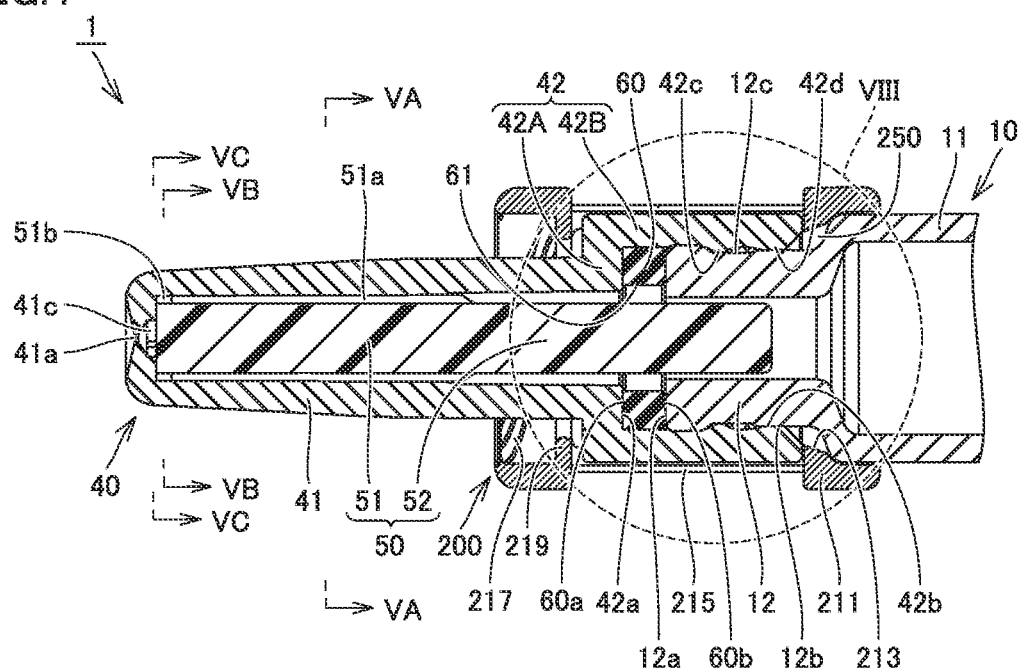
FIG. 4 is an enlarged view of a region IV shown in FIG. 2.

Each of engagement segments 211 extends rearward and curves along the outer circumference of connected portion 42 of nozzle 40. An opening 215 is provided at the central portion of engagement segment 211. At the rear end of engagement segment 211, engagement protrusion 213 is provided to protrude inward. As shown in FIGS. 2 and 4, engagement protrusion 213 protrudes toward a depression 250 provided between the rear end of nozzle 40 and barrel 10. Engagement protrusion 213 is engaged with the rear end of nozzle 40 to prevent connection adapter 200 from being moved in the front end direction.

Connection adapter 200 has an annular portion 219 protruding inward. Annular portion 219 is in abutment with a step on the front end side of connected portion 42 of nozzle 40 to prevent connection adapter 200 from being moved rearward.

As shown in FIG. 4, connection adapter 200 has a threaded portion 217 on its inner circumferential surface on the front end side. An increased-diameter portion 313 of vial adapter 300 at the rear end portion thereof is screwed into threaded portion 217.

As shown in FIG. 3, syringe-shaped spraying device 1 of the present embodiment includes vial adapter 300. Vial adapter 300 mainly has: a connection tube 311 located at the rear end portion of vial adapter 300 and connected to connection adapter 200; a transfer needle 321 to pierce a vial so as to suction the liquid medicine in the vial; and a holding portion 331 that holds an upper end of the vial. Details of a structure for holding the vial and vial adapter 300 will be described later.

Figure 5:
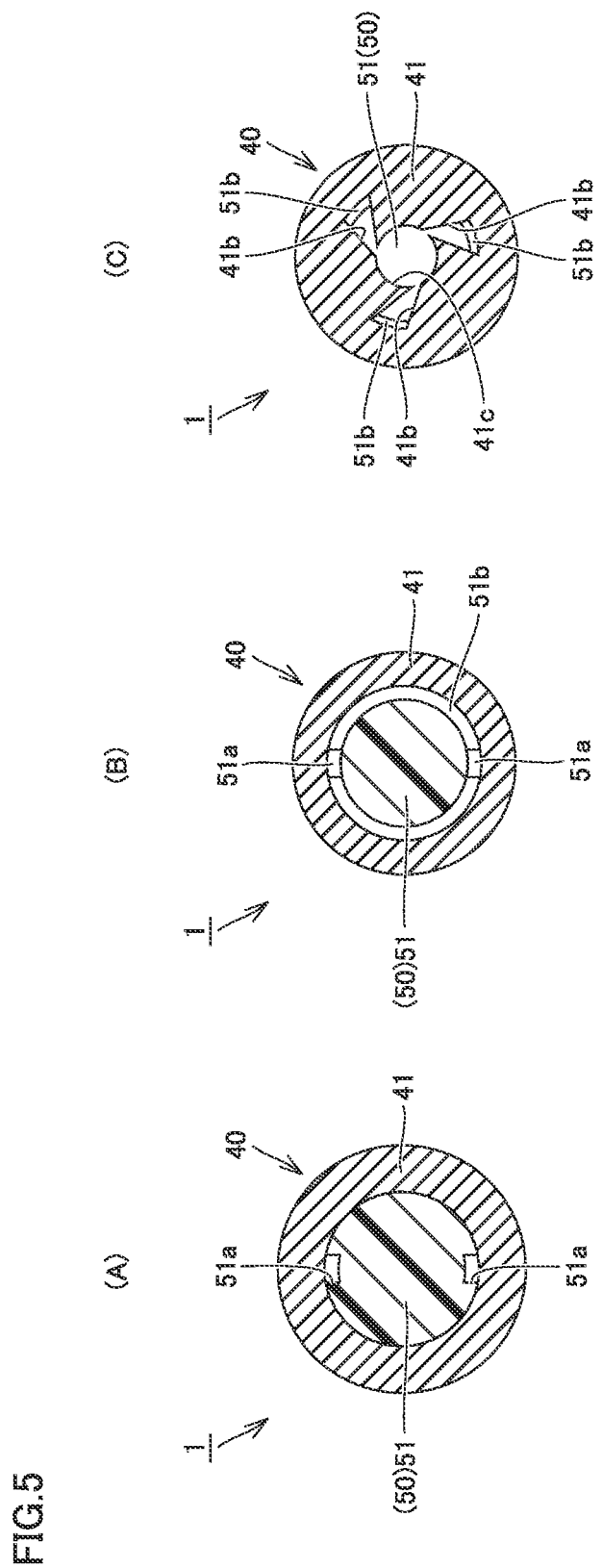
FIG. 5 is a cross sectional view taken along each of lines VA-VA, VB-VB, and VC-VC shown in FIG. 4.

FIG. 4 is an enlarged view of a region IV shown in FIG. 2. FIGS. 5 (A) to 5 (C) are cross sectional views taken along lines VA-VA, VB-VB, and VC-VC shown in FIG. 4, respectively. Referring to FIGS. 4 and 5, the following fully describes a configuration of the flow path for liquid medicine 100 inside nozzle 40 of syringe-shaped spraying device 1 according to the present embodiment.

As shown in FIG. 4, by providing through hole 61 in packing 60 interposed between barrel 10 and nozzle 40, the space inside barrel 10 and the space inside nozzle 40 communicate with each other via through hole 61. On the other hand, small-diameter portion 52 located at the rear end side of core 50 is inserted in and extends through packing 60 and is inserted in connecting portion 12 of barrel 10.

Here, the inner diameter of packing 60 and the inner diameter of connecting portion 12 are both larger than the outer diameter of small-diameter portion 52 of core 50. Thus, a minute clearance is formed between small-diameter portion 52 of core 50 and each of packing 60 and connecting portion 12, with the result that a flow path for liquid medicine 100 with a sufficiently small cross sectional area is defined by the clearance.

In the space inside nozzle 40, small-diameter portion 52 of core 50 is located within a space located on the rear end side of nozzle portion 41, i.e., at the portion adjacent to through hole 61 of packing 60. As described above, the outer diameter of small-diameter portion 52 is smaller than the inner diameter of nozzle portion 41. Thus, a minute clearance is also formed between small-diameter portion 52 of core 50 and nozzle portion 41, with the result that a flow path for liquid medicine 100 with a sufficiently small cross sectional area is defined by the clearance.

Moreover, the flow path for liquid medicine 100 is always in communication to allow liquid medicine 100 to flow from the front end side of nozzle 40 toward barrel 10. In other words, since a check valve, valve, or the like is not provided and the flow path for liquid medicine 100 is always formed, liquid medicine 100 can flow from the front end side of nozzle 40 to the base end side of nozzle 40.

As shown in FIGS. 4, 5 (A), and 5 (B), in the space inside nozzle 40, a flow path for liquid medicine 100 is defined within a space within which large-diameter portion 51 of core 50 is disposed, mainly by first groove portions 51a provided in the outer circumferential surface of large-diameter portion 51 and second groove portions 51b provided in the front end of large-diameter portion 51.

More specifically, since the outer diameter of large-diameter portion 51 is substantially equal to the inner diameter of nozzle portion 41 as described above, a flow path for liquid medicine 100 with a sufficiently small cross sectional area is defined by surfaces of first groove portions 51a and surfaces of second groove portions 51b as well as portions of the inner circumferential surface of nozzle portion 41 facing the surfaces of first groove portions 51a and the surfaces of second groove portions 51b. It should be noted that in the present embodiment, a pair of first groove portions 51a are provided at a pitch of 180° in the circumferential direction of core 50.

On the other hand, as shown in FIGS. 4 and 5 (C), a plurality of first flow path portions 41b radially extending to communicate with second groove portions 51b are provided at the front end (i.e., the bottom portion of nozzle portion 41) of nozzle 40 in which spraying hole 41a is provided. A second flow path portion 41c defined by a cylindrical space is provided in the bottom portion of a portion of nozzle portion 41 corresponding to the central portion of the plurality of first flow path portions 41b extending radially. Each of the plurality of first flow path portions 41b communicates with second flow path portion 41c. Second flow path portion 41c also communicates with spraying hole 41a.

Here, each of the plurality of first flow path portions 41b and second flow path portion 41c is formed to be sufficiently minute. Thus, a flow path for liquid medicine 100 with a sufficiently small cross sectional area is defined by the plurality of first flow path portions 41b and second flow path portion 41c.

As described above, in syringe-shaped spraying device 1 according to the present embodiment, since core 50 is accommodated inside nozzle 40, the cross sectional area of the flow path for liquid medicine 100 defined by nozzle 40 and core 50 is sufficiently small. Hence, the pressure of liquid medicine 100 in the flow path is increased, with the result that liquid medicine 100 is sprayed in the form of a mist from spraying hole 41a.

Figure 6:
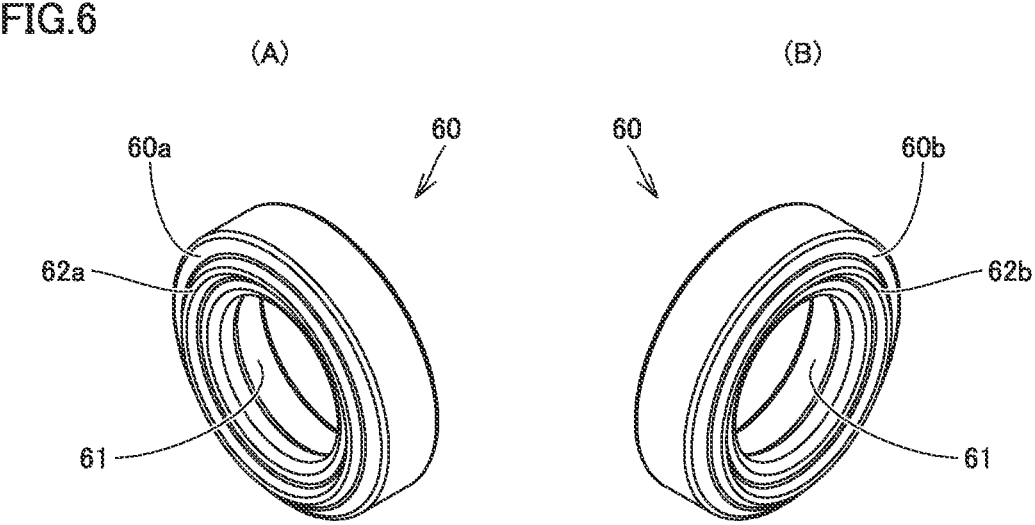
FIG. 6 is a perspective view of a packing shown in FIG. 2.
Figure 7:
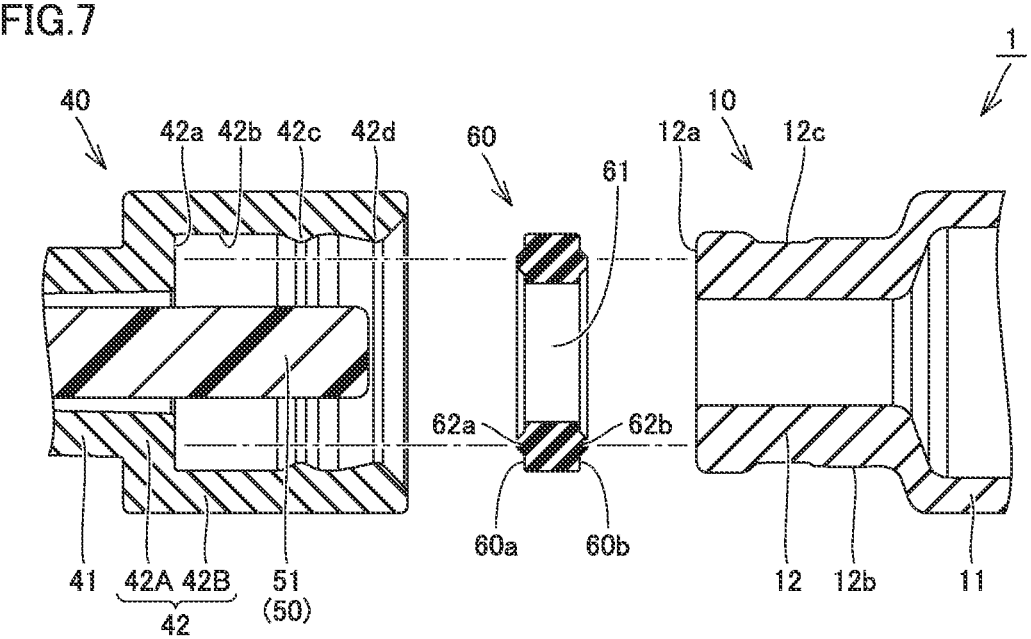
FIG. 7 is an exploded view showing a structure in which the packing shown in FIG. 2 is assembled.
Figure 8:
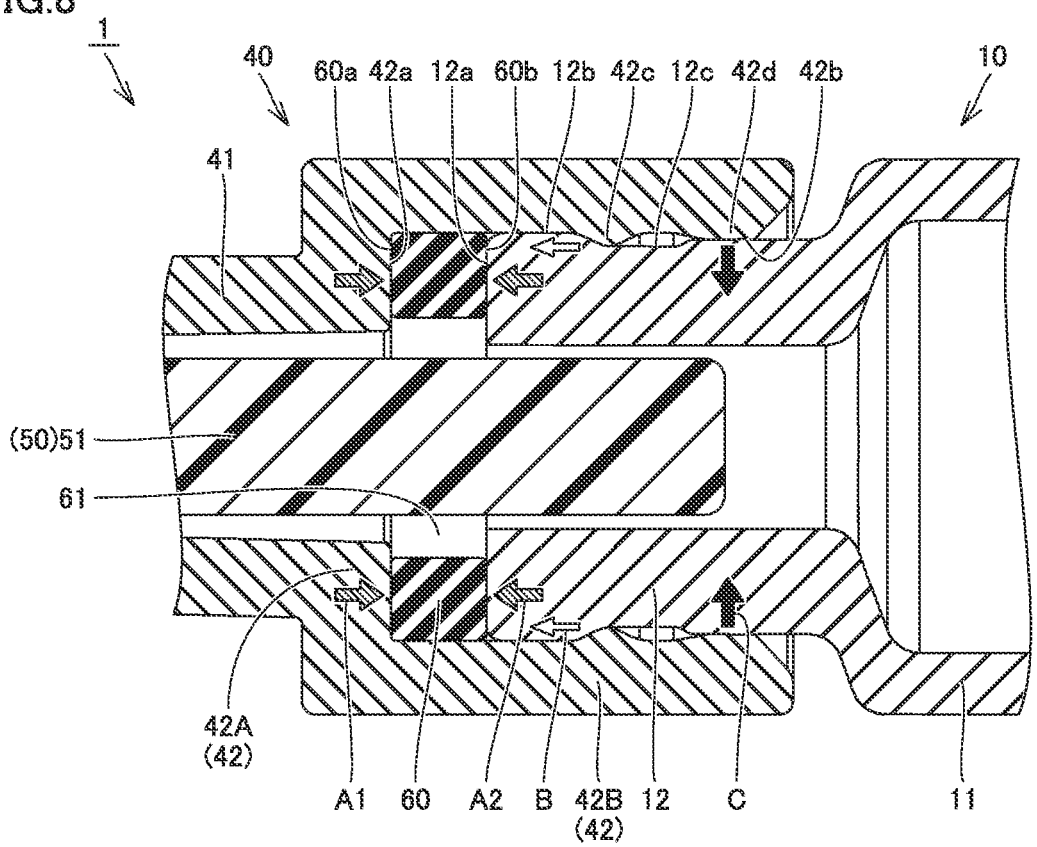
FIG. 8 is an enlarged view of a region VIII shown in FIG. 4.

Each of FIGS. 6 (A) and 6 (B) is a perspective view of the packing shown in FIG. 2. FIG. 7 is an exploded view showing a structure in which the packing is assembled. FIG. 8 is an enlarged view of a region VIII shown in FIG. 4. In FIG. 8, no connection adapter 200 is illustrated. Referring to FIGS. 6 to 8 as well as FIGS. 3 and 4, the following describes a structure in which nozzle 40 is assembled to barrel 10 in syringe-shaped spraying device 1 according to the present embodiment.

As shown in FIGS. 6 (A), 6 (B), and 7, packing 60, which has an annular shape and is provided with through hole 61, has a first main surface 60a and a second main surface 60b. First main surface 60a and second main surface 60b are a pair of main surfaces located in the axial direction. Each of first main surface 60a and second main surface 60b has an annular shape to surround through hole 61. First main surface 60a is provided with a first lip portion 62a having a protruding shape and extending along the circumferential direction. Second main surface 60b is provided with a second lip portion 62b extending along the circumferential direction.

As shown in FIG. 7, by sandwiching packing 60 between nozzle 40 and barrel 10 with first main surface 60a being disposed on the nozzle 40 side and second main surface 60b being disposed on the barrel 10 side, packing 60 is assembled to syringe-shaped spraying device 1. More specifically, packing 60 is assembled to barrel 10 and nozzle 40 with packing 60 being compressed by barrel 10 and nozzle 40 in the axial direction.

Here, as shown in FIGS. 3, 4, 7 and 8, connecting portion 12 of barrel 10 has a front end surface 12a having an annular shape and an outer circumferential surface 12b constituted of a substantially cylindrical surface. An annular recess portion 12c extending along the circumferential direction is provided at a predetermined position of outer circumferential surface 12b.

On the other hand, connected portion 42 of nozzle 40 has: a first facing wall portion 42A having an annular plate-like shape and located at the rear end of nozzle portion 41; and a second facing wall portion 42B having a substantially cylindrical shape and extending continuously from the outer edge of first facing wall portion 42A. First facing wall portion 42A has a first facing surface 42a facing front end surface 12a of connecting portion 12 of barrel 10, and second facing wall portion 42B has a second facing surface 42b facing outer circumferential surface 12b of connecting portion 12 of barrel 10.

First facing surface 42a has an annular shape, and second facing surface 42b is constituted of a substantially cylindrical surface. A first annular protrusion portion 42c extending along the circumferential direction and protruding inwardly in the radial direction is provided at a predetermined position of second facing surface 42b. A second annular protrusion portion 42d extending along the circumferential direction and protruding inwardly in the radial direction is provided at a portion of second facing surface 42b located on the rear end side of nozzle 40 with respect to the portion at which first annular protrusion portion 42c is provided.

As shown in FIG. 7, nozzle 40 is connected to barrel 10 by press-fitting connecting portion 12 of barrel 10 into connected portion 42 of nozzle 40. On this occasion, by interposing packing 60 between first facing surface 42a of nozzle 40 and front end surface 12a of barrel 10, packing 60 is sandwiched between first facing surface 42a and front end surface 12a.

As shown in FIG. 8, in the state after the assembly, first annular protrusion portion 42c provided at second facing surface 42b of connected portion 42 of nozzle 40 is engaged with annular recess portion 12c provided at outer circumferential surface 12b of connecting portion 12 of barrel 10. Accordingly, barrel 10 and nozzle 40 are restricted from being moved in directions in which they are separated further away from each other.

On this occasion, first main surface 60a of packing 60 is disposed on the nozzle 40 side, and second main surface 60b of packing 60 is disposed on the barrel 10 side. Therefore, after the assembly, first main surface 60a of packing 60 is in abutment with first facing surface 42a of nozzle 40, and second main surface 60b of packing 60 is in abutment with front end surface 12a of barrel 10.

Accordingly, packing 60 receives forces from first facing surface 42a of nozzle 40 and front end surface 12a of barrel 10 in opposite directions, i.e., directions of arrows A1 and A2 shown in the figure, with the result that packing 60 is compressed in the axial direction.

On the other hand, in response to a restoring force of compressed packing 60, annular recess portion 12c of barrel 10 receives a force from first annular protrusion portion 42c of nozzle 40 in a direction of arrow B shown in the figure (i.e., toward the packing 60 side).

Accordingly, nozzle 40 and barrel 10 are fixed in the axial direction, thereby connecting nozzle 40 to barrel 10.

It should be noted that on this occasion, each of first lip portion 62a and second lip portion 62b provided at packing 60 is compressed due to packing 60 being sandwiched between first facing surface 42a of nozzle 40 and front end surface 12a of barrel 10. Thus, first main surface 60a of packing 60 and first facing surface 42a of nozzle 40 are brought into close contact with each other, and second main surface 60b of packing 60 and front end surface 12a of barrel 10 are brought into close contact with each other, with the result that the space inside nozzle 40 is sealed from outside at these portions in a liquid-tight manner.

Here, in the case where nozzle 40 is fixed to barrel 10 only by engagement between annular recess portion 12c and first annular protrusion portion 42c, nozzle 40 and barrel 10 are fixed only in the axial direction as described above. Hence, when an external force is applied in a direction intersecting the axial direction, great looseness may occur between barrel 10 and nozzle 40.

Liquid medicine 100 may be leaked from between barrel 10 and nozzle 40 due to occurrence of such looseness during use as well as the increased pressure of liquid medicine 100 inside nozzle 40, particularly. Further, when such looseness occurs during use, nozzle 40 is axially displaced with respect to barrel 10 to cause displacement in the spraying direction of liquid medicine 100, with the result that liquid medicine 100 may be hindered from being administered to a target position.

To address this, in syringe-shaped spraying device 1 according to the present embodiment, second annular protrusion portion 42d extending along the circumferential direction and protruding inwardly in the radial direction is provided at the portion of second facing surface 42b located on the rear end side of nozzle 40 with respect to the portion at which first annular protrusion portion 42c is provided as described above, thereby suppressing the occurrence of looseness.

That is, as shown in FIG. 8, by providing second annular protrusion portion 42d at second facing surface 42b in pressure contact with outer circumferential surface 12b of connecting portion 12 entirely in the circumferential direction of connecting portion 12 of barrel 10, connecting portion 12 receives a force from second annular protrusion portion 42d of connected portion 42 in a direction of arrow C shown in the figure (i.e., inwardly in the radial direction). At this portion, nozzle 40 and barrel 10 are fixed in the radial direction.

Therefore, by employing this configuration, nozzle 40 and barrel 10 are fixed not only in the axial direction but also in the radial direction, with the result that nozzle 40 is connected to barrel 10 liquid-tightly and firmly. Therefore, even when an external force is applied to nozzle 40 or barrel 10 in a direction intersecting the axial direction, no great looseness occurs between barrel 10 and nozzle 40, with the result that occurrence of liquid leakage can be significantly suppressed.

This effect can be obtained not only in a non-used state but also in a used state in which the pressure of liquid medicine 100 is increased inside nozzle 40. That is, by employing the above-described configuration, nozzle 40 is connected to barrel 10 liquid-tightly and firmly, with the result that occurrence of liquid leakage can be suppressed even when the above-described external force is applied during use of syringe-shaped spraying device 1.

Further, according to syringe-shaped spraying device 1, looseness between barrel 10 and nozzle 40 can be suppressed as described above. Hence, nozzle 40 can be prevented in advance from being axially displaced with respect to barrel 10, thus avoiding displacement of the spraying direction of liquid medicine 100. Accordingly, liquid medicine 100 can be administered to a target position, advantageously.

Further, according to syringe-shaped spraying device 1, nozzle 40 can be liquid-tightly and firmly connected to barrel 10 by way of the very simple configuration in which second annular protrusion portion 42d is provided at second facing surface 42b of connected portion 42 of nozzle 40. Hence, syringe-shaped spraying device 1 with high performance can be provided at low cost without increasing manufacturing cost.

Figure 9:
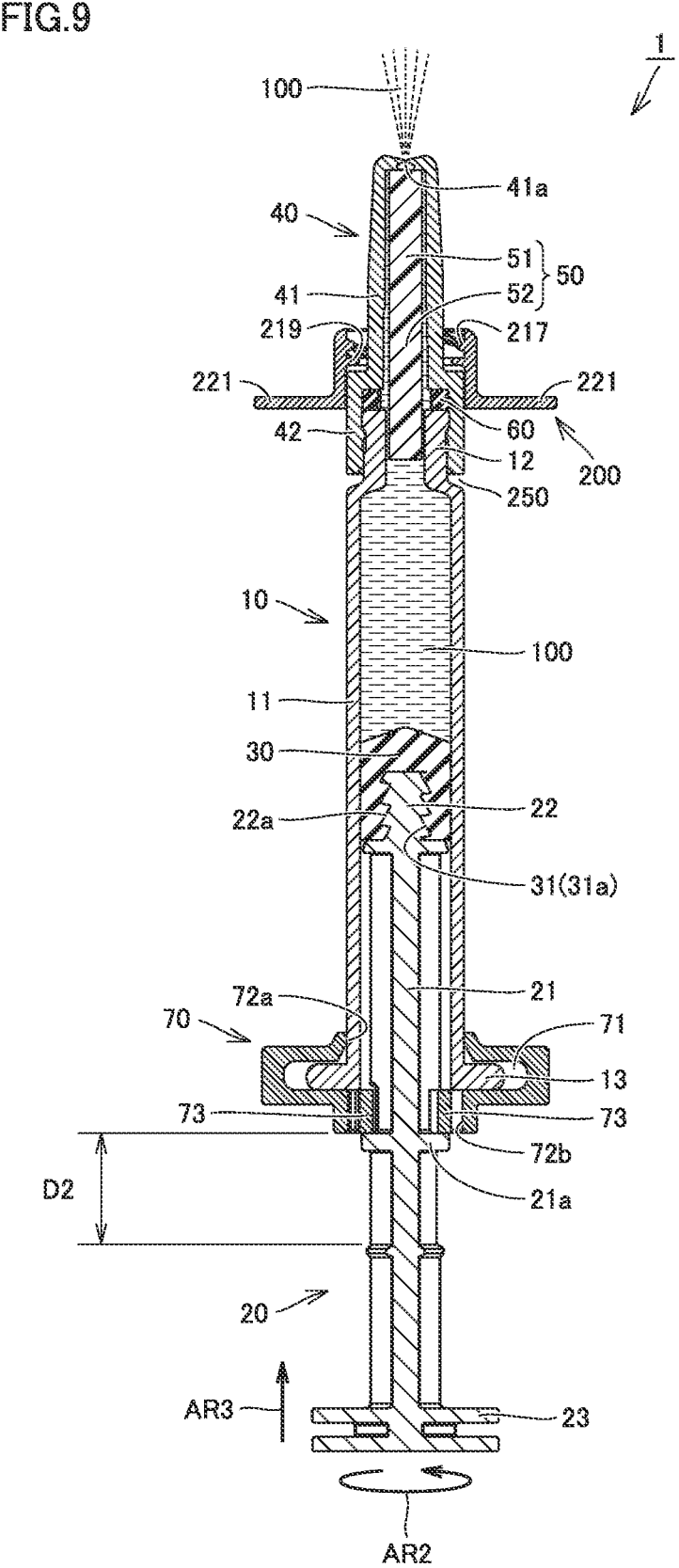
FIG. 9 is a cross sectional view showing the syringe-shaped spraying device at the time of completion of a first stage during administration.
Figure 10:
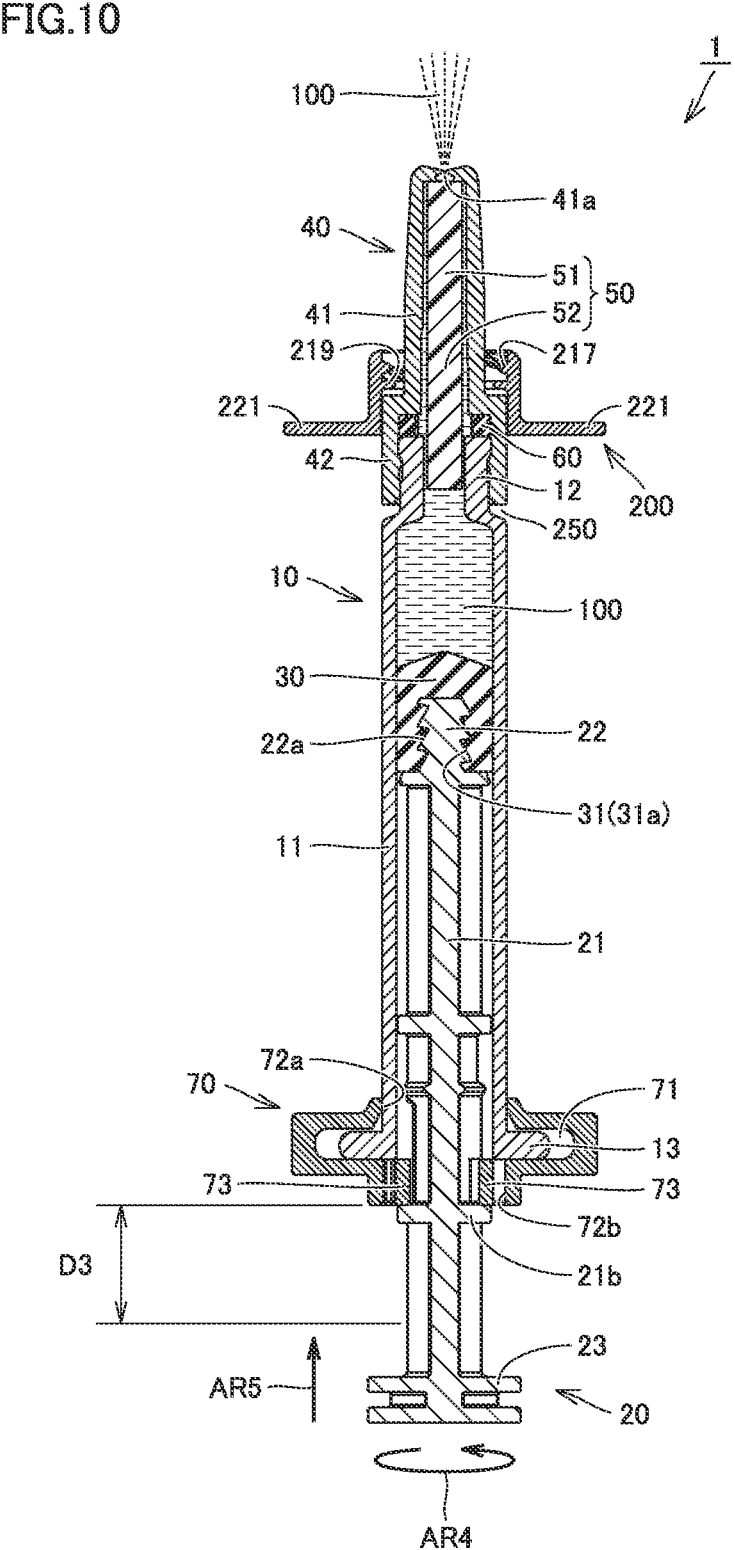
FIG. 10 is a cross sectional view showing the syringe-shaped spraying device at the time of completion of a second stage during the administration.
Figure 11:
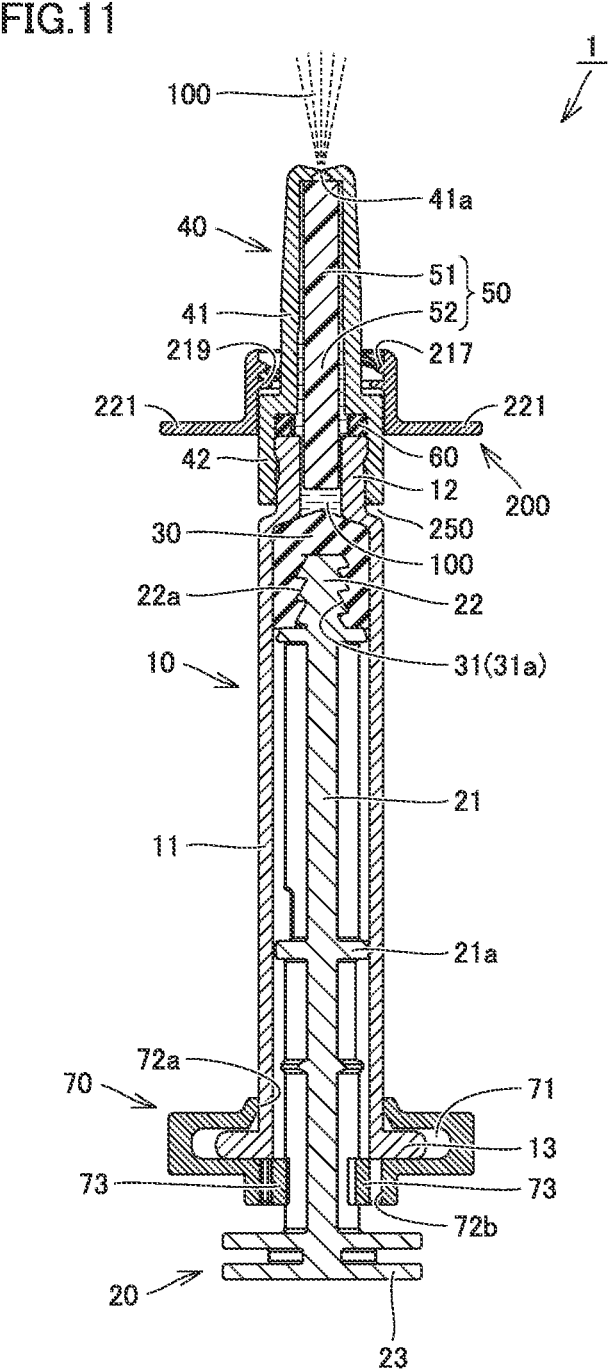
FIG. 11 is a cross sectional view showing the syringe-shaped spraying device at the time of completion of a third stage during the administration.

FIGS. 9 to 11 are cross sectional views showing respective states of the syringe-shaped spraying device shown in FIG. 1 at the times of completion of first to third stages during administration of the liquid medicine with the syringe-shaped spraying device. Referring to FIGS. 9 to 11 as well as FIG. 2 described above, the following describes a method of administering the suctioned liquid medicine using syringe-shaped spraying device 1 according to the present embodiment.

As shown in FIG. 2, in order to administer the liquid medicine using syringe-shaped spraying device 1, first, syringe-shaped spraying device 1 is brought into a standing posture such that nozzle 40 is located on the upper side in the vertical direction and plunger 20 is located on the lower side in the vertical direction. In this state, cap 80 is removed.

Next, as shown in FIG. 2, as the first stage, the user operates plunger 20 and pushes plunger 20 in a direction of arrow AR1 (i.e., toward the barrel 10 side) shown in the figure. On this occasion, the pair of first abutment portions 21a provided at rod portion 21 of plunger 20 are brought into abutment with the pair of stoppers 73 provided at finger grip 70, with the result that plunger 20 is stopped at the time when plunger 20 is moved by a distance D1 shown in the figure.

In the first stage, as shown in FIG. 9, due to the movement of plunger 20 by distance D1, air inside barrel 10 and nozzle 40 and an excess of liquid medicine 100 in barrel 10 (i.e., an amount obtained by subtracting, from the total amount of liquid medicine 100 in barrel 10, an amount of liquid medicine 100 to be administered to one nasal cavity, an amount of liquid medicine 100 to be administered to the other nasal cavity, and an amount of liquid medicine 100 to remain inside barrel 10 and nozzle 40 after completion of the administration) are sprayed from spraying hole 41a to the outside of syringe-shaped spraying device 1. Accordingly, barrel 10 and nozzle 40 are entirely filled with liquid medicine 100, thus completing preparation for administration of liquid medicine 100.

Next, as shown in FIG. 9, as the second stage, the user operates plunger 20 and rotates plunger 20 in a direction of arrow AR2 shown in the figure, with the result that the pair of first abutment portions 21a and the pair of stoppers 73 are brought out of abutment. Thereafter, the user inserts the front end of nozzle 40 into one nasal cavity, operates plunger 20, and pushes plunger 20 in a direction of arrow AR3 shown in the figure (i.e., toward the barrel 10 side). On this occasion, the pair of second abutment portions 21b provided at rod portion 21 of plunger 20 are brought into abutment with the pair of stoppers 73 provided at finger grip 70, with the result that plunger 20 is stopped at the time when plunger 20 is moved by a distance D2 shown in the figure.

When inserting the front end of nozzle 40 into the nasal cavity, guide 221 of the connecting portion is brought into abutment with the outer circumferential portion of the nasal cavity, thereby positioning the front end of nozzle 40 at an appropriate position in the nasal cavity. Further, since guide 221 is brought into abutment with the outer circumferential portion of the nasal cavity, nozzle 40 can be prevented from being inserted deeper than necessary into the nasal cavity.

In the second stage, as shown in FIG. 10, due to the movement of plunger 20 by distance D2, an amount of liquid medicine 100 corresponding to the predetermined amount of liquid medicine 100 to be administered to one nasal cavity is sprayed from spraying hole 41a to the outside of syringe-shaped spraying device 1. In this way, the administration of liquid medicine 100 to one nasal cavity is completed.

Next, as shown in FIG. 10, as the third stage, the user operates plunger 20 and rotates plunger 20 in a direction of arrow AR4 shown in the figure, with the result that the pair of second abutment portions 21b and the pair of stoppers 73 are brought out of abutment. Thereafter, the user inserts the front end of nozzle 40 into the other nasal cavity, operates plunger 20, and pushes plunger 20 in a direction of arrow AR5 shown in the figure (i.e., toward the barrel 10 side). On this occasion, the front end of gasket 30 is brought into abutment with an end portion of tubular portion 11 on the connecting portion 12 side of barrel 10, with the result that plunger 20 is stopped at the time when plunger 20 is moved by a distance D3 shown in the figure.

In the third stage, as shown in FIG. 11, due to the movement of plunger 20 by distance D3, an amount of liquid medicine 100 corresponding to the predetermined amount of liquid medicine 100 to be administered to the other nasal cavity is sprayed from spraying hole 41a to the outside of syringe-shaped spraying device 1. In this way, the administration of liquid medicine 100 to the other nasal cavity is completed.

In this way, the administration of liquid medicine 100 to the pair of nasal cavities of the patient is completed. With such a syringe-shaped spraying device 1 according to the present embodiment, it is possible to accurately administer a predetermined amount of liquid medicine 100 to each of the pair of nasal cavities of the patient while suppressing occurrence of liquid leakage during use. Since guide 221 is provided, the front end of nozzle 40 can be readily positioned at an appropriate position in a nasal cavity, with the result that liquid medicine 100 can be administered appropriately.

In the above-described embodiment of the present disclosure, it has been illustratively described that the flow path for liquid medicine with a sufficiently small cross sectional area is formed inside the nozzle by providing the core, which is accommodated inside the nozzle, with the pair of first groove portions extending in the axial direction and the second groove portions provided at the front end. However, the flow path does not necessarily need to be thus configured. That is, the flow path may be configured in any manner as long as the flow path for liquid medicine with a sufficiently small cross sectional area is formed by the nozzle and the core with the core being accommodated inside the nozzle.

The following describes a step of suctioning a liquid medicine into the syringe-shaped spraying device. For the step of suctioning, there are the following cases: a case (referred to as a "first suctioning step") of suctioning, into an empty barrel, a liquid medicine stored in a vial; and a case (referred to as a "second suctioning step") of temporarily introducing, into the vial, a liquid medicine or solution stored in the barrel in advance, mixing them with a medicine or liquid medicine stored in the vial so as to prepare a liquid medicine, and suctioning the prepared liquid medicine into the barrel. Hereinafter, these will be described sequentially.

Figure 12:
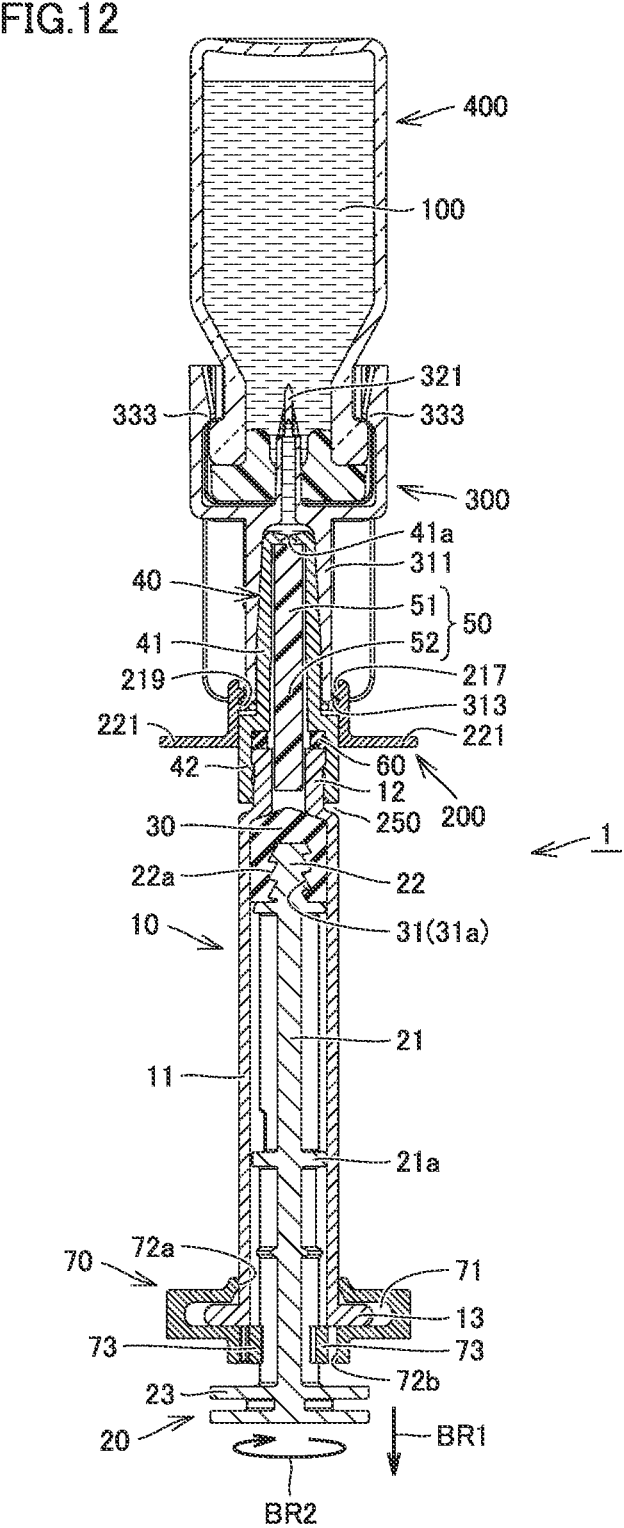
FIG. 12 is a cross sectional view showing the syringe-shaped spraying device at the start of suctioning of the liquid medicine in a first suctioning step.
Figure 13:
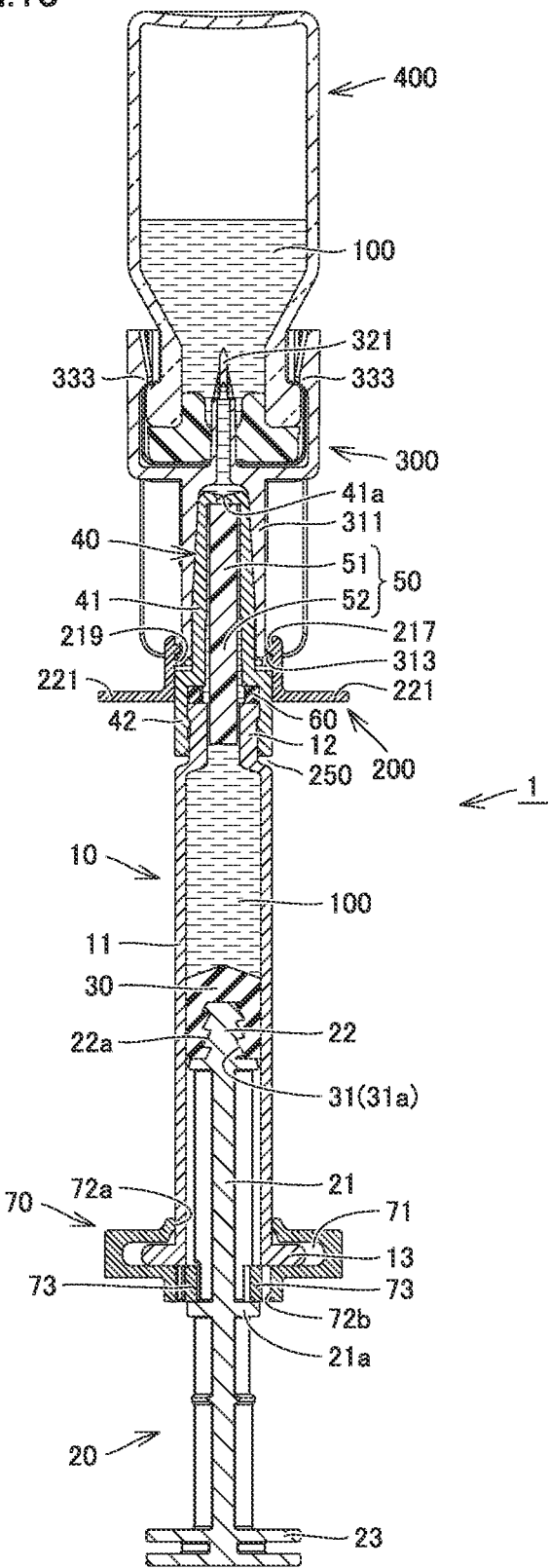
FIG. 13 is a cross sectional view showing the syringe-shaped spraying device at the end of suctioning of the liquid medicine in the first suctioning step.

FIG. 12 is a cross sectional view showing a state at the start of suctioning in the step of suctioning the liquid medicine from the vial using the syringe-shaped spraying device. FIG. 13 is a cross sectional view showing a state at the end of suctioning in the step of suctioning the liquid medicine from the vial using the syringe-shaped spraying device. Referring to FIGS. 12 and 13, the following describes: a more detailed structure for suctioning the liquid medicine in accordance with the first suctioning step using syringe-shaped spraying device 1 according to the present embodiment; and a method of suctioning the liquid medicine from the vial using syringe-shaped spraying device 1.

As shown in FIG. 12, vial adapter 300 is connected to connection adapter 200 of syringe-shaped spraying device 1. Vial adapter 300 is fixed to connection adapter 200 by screwing, into threaded portion 217 of connection adapter 200, increased-diameter portion 313 provided at the rear end portion of connection tube 311 of vial adapter 300. By screwing increased-diameter portion 313 of vial adapter 300 into threaded portion 217 of connection adapter 200, vial adapter 300 can be securely and firmly fixed to connection adapter 200. The inner surface of connection tube 311 of vial adapter 300 overlaps with and is in close contact with the outer circumferential surface of nozzle 40 in the state in which vial adapter 300 is fixed to connection adapter 200. By screwing increased-diameter portion 313 into threaded portion 217, the inner surface of connection tube 311 can be securely brought into close contact with the outer circumferential surface of nozzle 40.

Vial adapter 300 has a pair of retainers 333 at positions facing each other with transfer needle 321 being interposed therebetween. Each of retainers 333 has a wedge shape protruding inward in a direction toward the rear side. Retainer 333 is provided on the inner surface side of a cantilever-shaped tongue segment 335. Tongue segment 335 can be deformed outward due to its elasticity. In a state in which tongue segment 335 is deformed outward, retainer 333 is biased inward.

In a state in which vial adapter 300 is attached to connection adapter 200 and the syringe-shaped spraying device main body, vial 400 is attached to vial adapter 300. On this occasion, transfer needle 321 penetrates the rubber plug of vial 400. Retainer 333 is engaged with the neck portion of vial 400 on its inner side to prevent vial 400 from falling out.

As shown in FIG. 3, vial adapter 300 is provided with three pairs of supporting segments 337 that are brought into abutment with the outer circumferential surface of the neck portion of vial 400 to stabilize vial 400. The three pairs of supporting segments 337 are provided such that corresponding supporting segments 337 are at symmetrical positions with respect to transfer needle 321. Since the pair of retainers 333 and the three pairs of supporting segments 337 are brought into abutment with vial 400, vial 400 can be stably held by vial adapter 300.

As shown in FIG. 12, transfer needle 321 penetrates the rubber plug of vial 400 and is positioned in the liquid medicine stored in vial 400. Transfer needle 321 is in the form of a steeple and is hollow. The liquid medicine can be suctioned into transfer needle 321 through an opening provided in a side surface of the front end portion of transfer needle 321. The penetration of transfer needle 321 through the rubber plug of vial 400 also contributes to stable holding of vial 400 by vial adapter 300.

Syringe-shaped spraying device 1 is brought into a standing posture such that vial 400 in the state shown in FIG. 12 is located on the upper side in the vertical direction and plunger 20 is located on the lower side in the vertical direction, and in this state, plunger 20 is drawn in a direction of BR1. Thus, liquid medicine 100 in vial 400 is suctioned into barrel 10 as shown in FIG. 13.

On this occasion, since the pair of stoppers 73 provided on finger grip 70 are sequentially brought into abutment with second abutment portion 21b and first abutment portion 21a, plunger 20 is further drawn in the direction of BR1 while rotating plunger 20 in a direction of BR2 for the sake of disengagement. In this way, an amount of liquid medicine 100 required for administration can be suctioned into barrel 10.

Finger grip 70 is provided to be attachable to and detachable from barrel 10. Finger grip 70 may be removed when suctioning liquid medicine 100.

Figure 14:
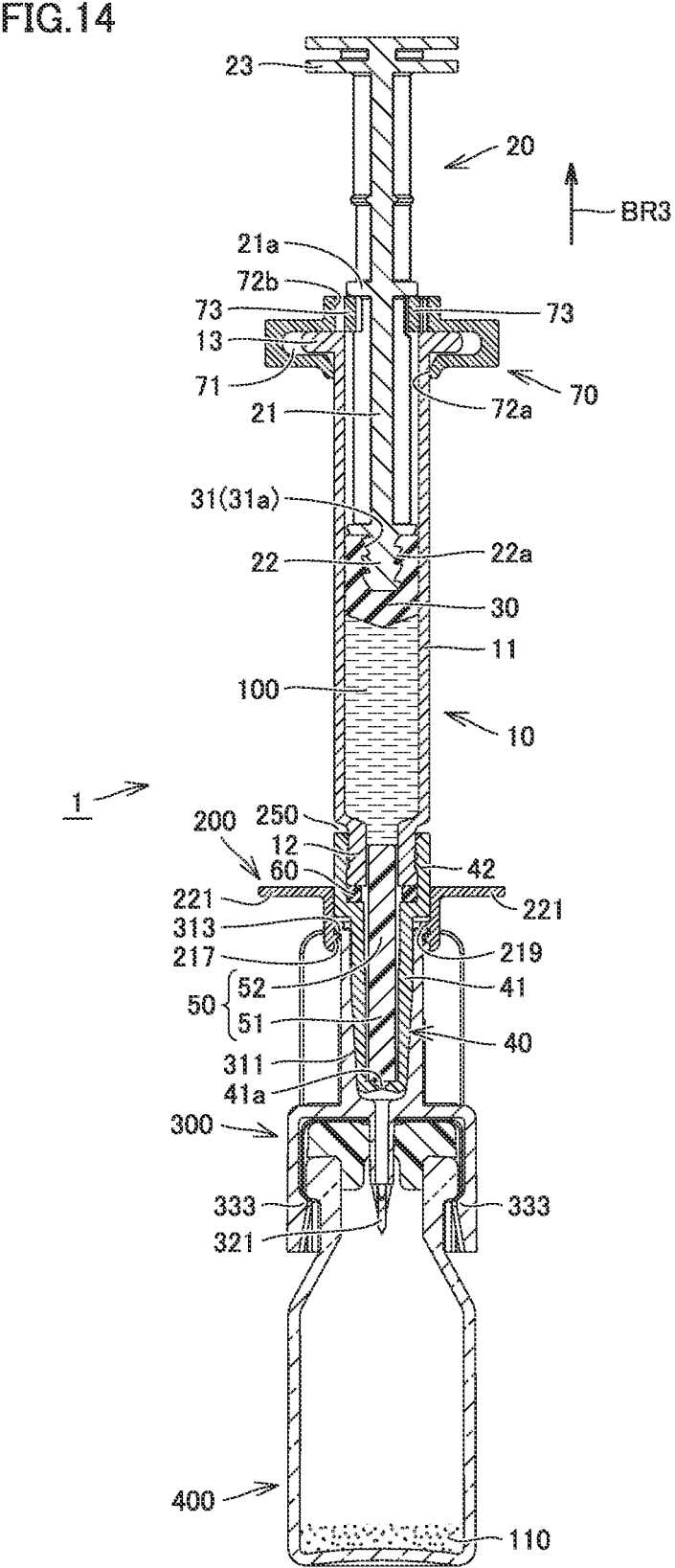
FIG. 14 is a cross sectional view showing the syringe-shaped spraying device before the start of introduction in a step of introducing the liquid medicine into a vial in a second suctioning step.
Figure 15:
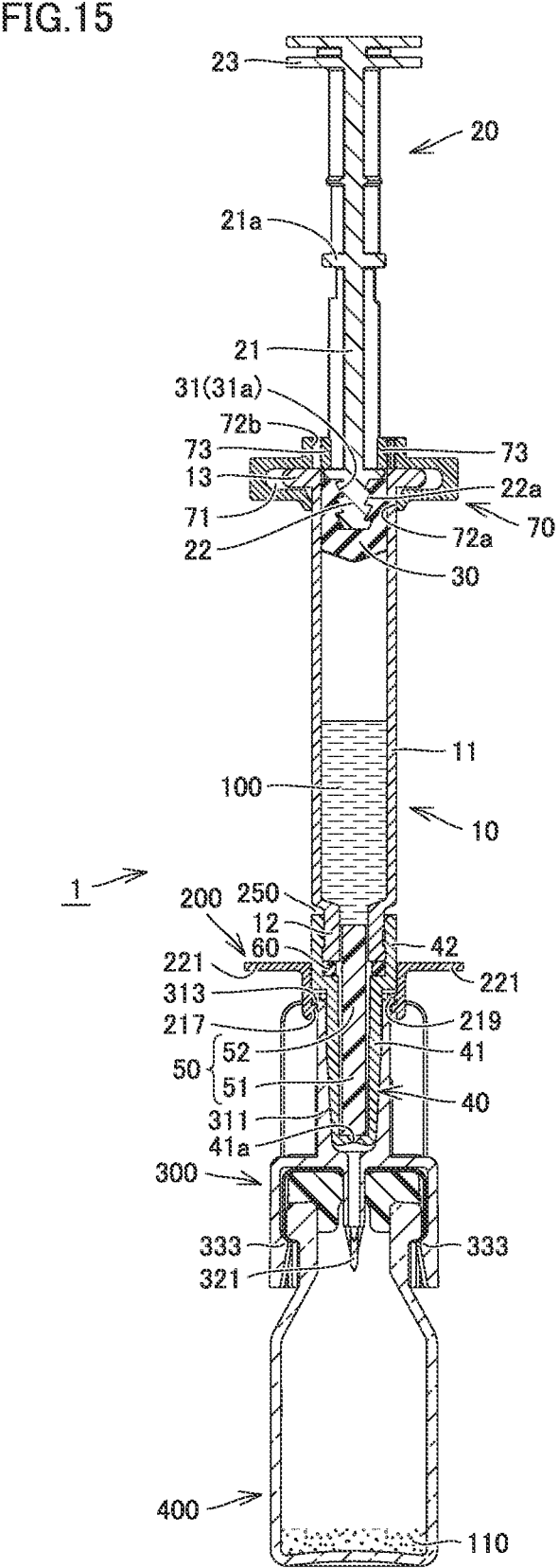
FIG. 15 is a cross sectional view showing the syringe-shaped spraying device at the start of introduction in the step of introducing the liquid medicine into the vial in the second suctioning step.
Figure 16:
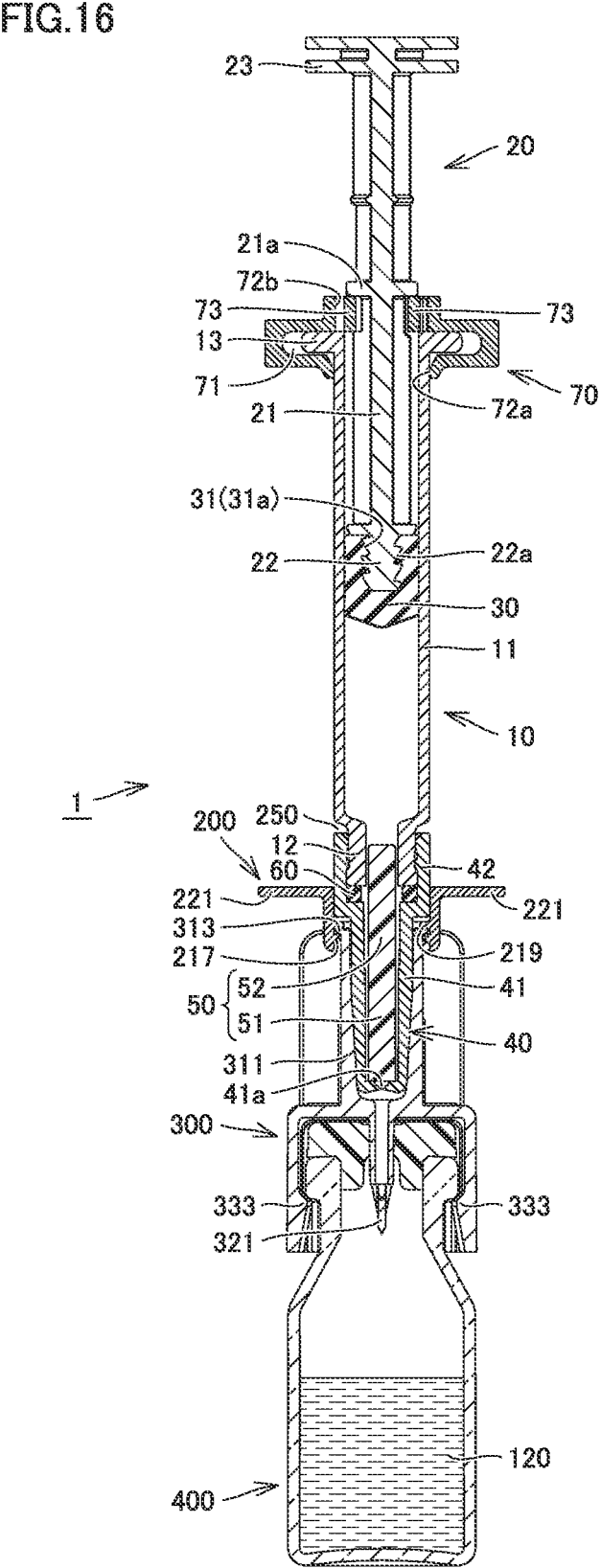
FIG. 16 is a cross sectional view showing the syringe-shaped spraying device at the end of introduction in the step of introducing the liquid medicine into the vial in the second suctioning step.
Figure 17:
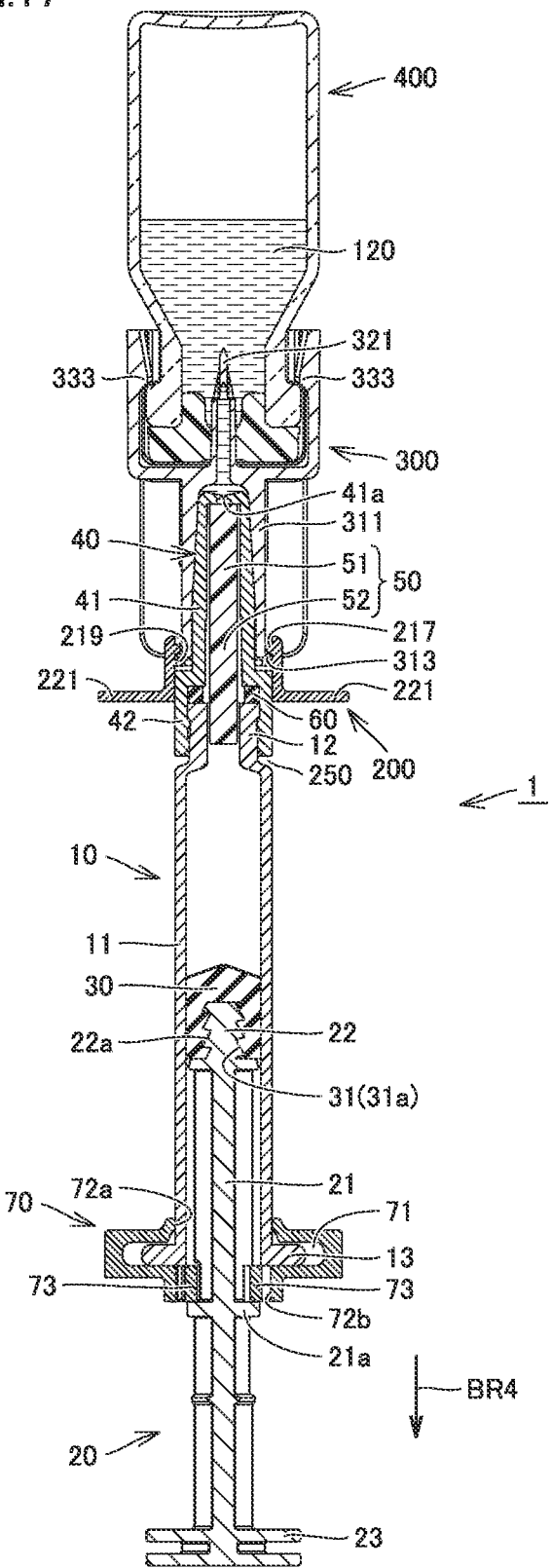
FIG. 17 is a cross sectional view showing the syringe-shaped spraying device at the start of suctioning of the liquid medicine in the second suctioning step.

FIG. 14 is a cross sectional view showing a state before the start of introduction in the step of introducing the liquid medicine from the syringe-shaped spraying device into the vial. FIG. 15 is a cross sectional view showing a state at the start of introduction in the step of introducing the liquid medicine from the syringe-shaped spraying device into the vial. FIG. 16 is a cross sectional view showing a state at the end of introduction in the step of introducing the liquid medicine from the syringe-shaped spraying device into the vial. FIG. 17 is a cross sectional view showing a state at the start of suctioning in the step of suctioning, from the vial using the syringe-shaped spraying device, the liquid medicine prepared in the vial. Referring to FIGS. 14 to 17, the following describes a method of suctioning the liquid medicine in accordance with the second suctioning step using syringe-shaped spraying device 1 according to the present embodiment.

As shown in FIG. 14, in syringe-shaped spraying device 1 used in the second suctioning step, liquid medicine 100 or solution is stored in barrel 10 in advance. That is, the syringe-shaped spraying device used in the second suctioning step is a pre-filled syringe. Further, a solid medicine 110 is stored in vial 400. A liquid medicine may be stored in vial 400 instead of solid medicine 110.

Vial adapter 300 is connected to connection adapter 200 of syringe-shaped spraying device 1. By screwing, into threaded portion 217 of connection adapter 200, increased-diameter portion 313 provided at the rear end portion of connection tube 311 of vial adapter 300, vial adapter 300 is fixed to connection adapter 200. By screwing increased-diameter portion 313 of vial adapter 300 into threaded portion 217 of connection adapter 200, vial adapter 300 can be securely and firmly fixed to connection adapter 200.

The inner surface of connection tube 311 of vial adapter 300 overlaps with and is in close contact with the outer circumferential surface of nozzle 40 in the state in which vial adapter 300 is fixed to connection adapter 200. By screwing increased-diameter portion 313 into threaded portion 217, the inner surface of connection tube 311 can be securely brought into close contact with the outer circumferential surface of nozzle 40.

In a state in which vial adapter 300 is attached to connection adapter 200 and the syringe-shaped spraying device main body, vial 400 is attached to vial adapter 300. On this occasion, transfer needle 321 penetrates the rubber plug of vial 400. Retainer 333 is engaged with the neck portion of vial 400 on its inner side to prevent vial 400 from falling out.

As shown in FIG. 14, transfer needle 321 penetrates the rubber plug of vial 400. As shown in FIG. 14, since the posture is such that vial 400 is located on the lower side in the vertical direction, the front end of transfer needle 321 is located in vial 400 at a portion at which air is present. In this state, when plunger 20 is drawn in a direction of BR3 (upper side in FIG. 14), the air in vial 400 is suctioned into barrel 10, thus resulting in negative pressure in vial 400. Plunger 20 is drawn until the base portion of gasket 30 is brought into abutment with stopper 73. FIG. 15 shows a state in which the base portion of gasket 30 is in abutment with stopper 73.

Since the pressure in vial 400 is negative pressure, when plunger 20 is released in the state of FIG. 15, plunger 20 is moved frontward due to the negative pressure and liquid medicine 100 in barrel 10 is moved into vial 400. FIG. 16 shows a state of completion of the movement of the whole of liquid medicine 100 in barrel 10 into vial 400.

In the state shown in FIG. 16, liquid medicine 100 stored in barrel 10 and solid medicine 110 stored in vial 400 are mixed with each other. By vibrating vial 400 in this state, solid medicine 110 is completely dissolved in liquid medicine 100, thereby completing preparation of a liquid medicine 120.

Thereafter, as shown in FIG. 17, syringe-shaped spraying device 1 is brought into a standing posture such that vial 400 is located on the upper side in the vertical direction and plunger 20 is located on the lower side in the vertical direction, and in this state, plunger 20 is drawn in a direction of BR4. Thus, liquid medicine 120 prepared in vial 400 is suctioned into barrel 10.

In the description of the second suctioning step, it has been mainly described that liquid medicine 100 is stored in barrel 10; however, a liquid medicine can be prepared in vial 400 by the same step also when a solution is stored in barrel 10. Further, a liquid medicine can be prepared in vial 400 by the same step also when a liquid medicine is stored in vial 400.

Liquid medicine 100, 120 can be suctioned into barrel 10 by the first suctioning step or the second suctioning step. Thereafter, vial 400 and vial adapter 300 are removed from the syringe-shaped spraying device main body. Liquid medicine 100 suctioned is administered to the user using syringe-shaped spraying device 1 in accordance with the procedure described above.

The embodiments and examples disclosed herein are illustrative and non-restrictive in any respect. The scope of the present invention is defined by the terms of the claims, and is intended to include any modifications within the scope and meaning equivalent to the terms of the claims.

INDUSTRIAL APPLICABILITY

The syringe-shaped spraying device of the present disclosure has industrial applicability as a syringe-shaped spraying device in which a syringe can be supplied with a liquid medicine by suctioning the liquid medicine from a nozzle.

REFERENCE SIGNS LIST

1: syringe-shaped spraying device; 10: barrel; 11: tubular portion; 12: connecting portion; 12a: front end surface; 12b: outer circumferential surface; 12c: annular recess portion; 13: flange portion; 20: plunger; 21: rod portion; 21*a*: first abutment portion; 21*b*: second abutment portion; 22: coupler portion; 22*a*: external thread; 23: flange portion; 30: gasket; 31: axial hole portion; 31*a*: internal thread; 40: nozzle; 41: nozzle portion; 41*a*: spraying hole; 41*b*: first flow path portion; 41*c*: second flow path portion; 42: connected portion; 42A: first facing wall portion; 42B: second facing wall portion; 42*a*: first facing wall portion; 42*b*: second facing surface; 42*c*: first annular protrusion portion; 42*d*: second annular protrusion portion; 50: core; 51: large-diameter portion; 51*a*: first groove portion; 51*b*: second groove portion; 52: small-diameter portion; 60: packing; 60*a*: first main surface; 60*b*: second main surface; 61: through hole; 62*a*: first lip portion; 62*b*: second lip portion; 70: finger grip; 71: accommodation space; 72*a*: first insertion portion; 72*b*: second insertion portion; 73: stopper; 80: cap; 100: liquid medicine; 110: medicine; 120: liquid medicine; 200: connection adapter; 211: engagement segment; 213: engagement protrusion; 215: opening; 217: threaded portion; 219: annular portion; 221: guide; 300: vial adapter; 311: connection tube; 313: increased-diameter portion; 321: transfer needle; 331: holding portion; 333: retainer; 335: tongue segment; 337: supporting segment; 400: vial.

The invention claimed is:

1. A syringe-shaped spraying device comprising:
a syringe-shaped spraying device main body including a barrel that stores a liquid medicine, a plunger having a front end inserted in the barrel with a gasket being attached to the front end, and a nozzle having a front end and a rear end, that is provided with a spraying hole for spraying the liquid medicine at the front end of the nozzle and that is connected to a front end of the barrel by inserting the front end of the barrel into an opening provided at the rear end of the nozzle;
a vial adapter having a transfer needle to pierce a vial that stores a liquid medicine so as to suction the liquid medicine; and
a connection adapter that is attached to the syringe-shaped spraying device main body and that connects the vial adapter to the syringe-shaped spraying device main body, wherein
a depression is formed between the rear end of the nozzle and the barrel, and the connection adapter has an engagement protrusion protruding toward the depression, and
the connection adapter is locked to the syringe-shaped spraying device main body with the engagement protrusion being engaged with the rear end of the nozzle.

2. The syringe-shaped spraying device according to claim 1, wherein the connection adapter has a guide extending in a direction orthogonal to a direction in which the nozzle extends.

3. The syringe-shaped spraying device according to claim 1, wherein the connection adapter has a threaded portion, and the vial adapter is connected to the connection adapter using the threaded portion.

* * * * *